(12) United States Patent
Hellström et al.

(10) Patent No.: US 8,022,267 B2
(45) Date of Patent: Sep. 20, 2011

(54) HYDROENTANGLED NONWOVEN FABRIC, METHOD OF MAKING IT AND ABSORBENT ARTICLE CONTAINING THE FABRIC

(75) Inventors: Jeanette Hellström, Göteborg (SE);
Ulrika Persson, Kungsbacka (SE);
Niclas Hörle, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 310 days.

(21) Appl. No.: 12/295,087

(22) PCT Filed: Mar. 30, 2006

(86) PCT No.: PCT/SE2006/000392
§ 371 (c)(1),
(2), (4) Date: Sep. 29, 2008

(87) PCT Pub. No.: WO2007/114742
PCT Pub. Date: Oct. 11, 2007

(65) Prior Publication Data
US 2009/0259208 A1    Oct. 15, 2009

(51) Int. Cl.
*A61F 13/15* (2006.01)
*A61F 13/20* (2006.01)

(52) U.S. Cl. .................. 604/367; 604/383; 604/385.101; 428/134

(58) Field of Classification Search .......... 428/131–136; 604/367, 383, 385.01
See application file for complete search history.

(56) References Cited

U.S. PATENT DOCUMENTS

| | | | |
|---|---|---|---|
| 4,840,829 A * | 6/1989 | Suzuki et al. | ................. 428/131 |
| 5,171,238 A | 12/1992 | Kajander | |
| 6,270,623 B1 | 8/2001 | Goda et al. | |
| 6,375,889 B1 | 4/2002 | Holmes et al. | |
| 2003/0125687 A1 | 7/2003 | Gubernick et al. | |
| 2005/0148969 A1 | 7/2005 | Damay et al. | |

FOREIGN PATENT DOCUMENTS

| | | |
|---|---|---|
| CA | 841938 | 5/1970 |
| CA | 2346889 | 4/2000 |
| EP | 0223614 | 5/1987 |
| EP | 0418493 | 3/1991 |
| WO | WO 0171081 A1 * | 9/2001 |
| WO | 01/88261 | 11/2001 |

* cited by examiner

*Primary Examiner* — Melanie Hand
(74) *Attorney, Agent, or Firm* — Drinker Biddle & Reath LLP

(57) ABSTRACT

A nonwoven fabric comprising at least 50% by weight microfibers having a fineness of 1.0 dtex or less and a length of at least 30 mm and having been combined by hydroentangling. The fabric is apertured by said hydroentangling, and has been carded before hydroentangling. The fabric may be used as a topsheet material on an absorbent article.

27 Claims, 5 Drawing Sheets

HYDROENTANGLED NONWOVEN FABRIC, METHOD OF MAKING IT AND ABSORBENT ARTICLE CONTAINING THE FABRIC

RELATED APPLICATION DATA

This application is a §371 National Stage Application of PCT International Application No. PCT/SE2006/000392 filed Mar. 30, 2006.

TECHNICAL FIELD

The present invention refers to a nonwoven fabric comprising microfibers having a fineness of 1 dtex or less and having been combined by hydroentangling. The invention further refers to a method for making the nonwoven fabric. The present invention also refers to an absorbent article comprising the nonwoven fabric as a topsheet material.

BACKGROUND OF THE INVENTION

Hydroentangling or spunlacing is a technique introduced during the 1970'ies, see e.g. CA patent no. 841 938. The method involves forming a fibre web, which is either drylaid or wetlaid, after which the fibres are entangled by means of very fine water jets under high pressure. Several rows of water jets are directed against the fibre web, which is supported by a movable wire or perforated drum. The entangled fibre web is then dried. The fibres that are used in the material can be natural fibres, especially cellulosic pulp fibres, manmade staple fibres, which may be synthetic, e.g. polyester, polyamide, polyethylene, polypropylene, or regenerated staple fibres, e.g. viscose, rayon, lyocell or the like, and mixtures of pulp fibres and staple fibres. Hydroentangled materials can be produced in high quality to a reasonable cost and depending on the type of fibers used they possess desired properties like high liquid absorption, liquid distribution, liquid inlet, softness etc. They can e.g. be used as wiping material for household or industrial use, as disposable materials in medical care, and in hygiene articles as topsheet materials and absorbent components etc.

Topsheet materials in absorbent articles like sanitary napkins, diapers, pant diapers, incontinence guards etc. are designed to distribute and move body fluids rapidly through them and into an underlying absorbent structure for storage. The more rapid, directionally controlled and thorough this transport is, the drier and cleaner the surface of the article and the greater is the comfort experienced by the wearer. Nonwoven fabrics used as topsheet often need to be modified, for example apertured, corrugated and/or treated with fluid modifying agents, such as surfactants or softeners in order to maximize its fluid handling and comfort properties. The softness of nonwoven fabrics can be increased by mechanical and/or chemical treatment.

The skin is sensitive to the changes in force required to deflect the fibres that are in contact with the skin surface. The bending stiffness of a fibre is a function of its fineness. Accordingly, for a given polymer, a decrease in filament linear fineness tends to increase its perception of softness. Spunbond and meltblown technologies are available that produce fine filaments having a fineness of 1 dtex or less. There are also known other techniques for producing nonwoven materials comprising microfibers.

U.S. Pat. No. 6,270,623 discloses an method of making an apertured nonwoven fabric useful as a topsheet on an absorbent article, wherein a wet sheet is formed from a wet slurry containing a mixture of pulp fibres and synthetic microfibers having a length between 7 and 30 mm and a fineness of 0.1-0.8 denier. The sheet is subjected to hydroentanglement. The web is apertured either as a result of hydroentanglement or by piercing with needles.

US 2003/0125687 discloses a multiple zone apertured web used as topsheet on an absorbent article. The web has at least two distinct zones of different hole sizes. The apertures may be formed by placing the web on a patterned support member and then subject it to high fluid pressure, which means hydroentanglement.

EP-A-0 418 493 discloses a nonwoven composite fabric comprising one layer selected from a web of textile fibres and a net of polymeric filaments and at least one web of meltblown microfibers, combined by hydroentangling. The web may be apertured by hydroentangling and holes of different sizes may be produced. The fabric may be used as a topsheet on an absorbent article.

US 2005/0148969 describes a combined cover layer and absorbent layer for an absorbent pantiliner comprising a mixture of hydrophilic and hydrophobic microfibers, wherein a larger quantity of hydrophobic microfibers than hydrophilic microfibers are located at the top surface of the cover layer.

However there still exists a need for improvement of nonwoven fabrics, especially adapted as topsheet materials on absorbent articles, with respect to softness, liquid inlet and rewet properties.

SUMMARY OF THE INVENTION

It is an object of the present invention to provide nonwoven fabrics comprising microfibers and which combines properties as softness, liquid inlet and rewet, thus making it especially useful as a topsheet material on an absorbent article. The fabric according to the invention comprises at least 50% by weight of microfibers having a fineness of 1 dtex or less and a length of at least 30 mm, preferably at least 32 mm and more preferably at least 35 mm, and having been combined by hydroentangling. The fabric is apertured by said hydroentangling.

In one aspect of the invention the fabric comprises at least 70% and preferably at least 90% of said microfibers. According to one embodiment it comprises 100% manmade fibers and is free from natural fibers, like pulp fibers. In one embodiment it comprises 100% of said microfibers.

In a further aspect of the invention the fabric comprises apertures of at least two different sizes arranged in discrete zones. The apertures of at least two different sizes may be arranged in discrete areas of the fabric in a repeated pattern in the machine direction or the cross direction of the fabric or both in machine and cross direction.

The size of each aperture may vary from 0.1 to 8 $mm^2$, preferably between 0.8 and 4 $mm^2$. The open area of the apertured fabric may be between 10 and 50%, preferably between 20 and 40%.

The fabric may have a basis weight of between 16 and 60 $g/m^2$, preferably between 20 and 40 $g/m^2$.

In still another embodiment all microfibers are hydrophobic microfibers.

The fabric may contain a wetting agent

In one aspect of the invention the fabric comprises up to 50% by weight man made fibers having a fineness of more than 1.0 dtex and up to 5.0 dtex. Said fibers having a fineness of more than 1.0 dtex are predominantly located on one side of the fabric, while the opposite side of the fabric predominantly comprises microfibers.

The invention further refers to a method of making a nonwoven fabric, comprising the steps of:

forming a carded fibrous web comprising at least 50% by weight microfibers having a fineness of 1.0 dtex or less and a length of at least 30 mm;

hydroentangling the carded fibrous web using an aperturing support member at the hydroentangling to produce an apertured hydroentangled nonwoven fabric.

In one embodiment the method uses an aperturing support member at the hydroentangling which produces apertures of at least two different sizes arranged in discrete zones of the hydroentangled fabric.

In one aspect of the invention the method uses an aperturing support member which produces apertures of different sizes arranged in discrete areas of the hydroentangled web, in a repeated pattern in the machine direction or in the cross direction of the web or both in machine and cross direction.

In a further embodiment the method comprises the steps of forming a carded fibrous web comprising at least 50% by weight microfibers and no more than 50% by weight other fibers having a fineness of more then 1.0 dtex and a length of at least 30 mm, preferably at least 32 mm and more preferably at least 35 mm, said microfibers and other fibers being applied in a layered configuration, hydroentangling the carded web to produce a hydroentangled nonwoven fabric comprising predominantly microfibers on one side and predominantly other fibers on the opposite side.

In one aspect of the invention the carded fibrous web is hydroentangled with a hydroentangling pressure of between 70 and 120 bars.

The invention further refers to an absorbent article such as a sanitary napkin, pantiliner, incontinence guard, baby diaper, pant diaper, sanitary pant and the like, said article comprising a topsheet arranged on the wearer facing side of an absorbent structure wherein the topsheet comprises a carded, hydroentangled and apertured nonwoven fabric as described above.

In one embodiment the topsheet comprises apertures of at least two different sizes arranged in discrete zones of the topsheet. Apertures of a relatively larger size may be arranged in a central portion of the article intended to form the wetting area, while apertures of a relatively smaller size may be arranged in an area surrounding the wetting area.

In a further embodiment said nonwoven fabric forming the topsheet comprises no more than 50% by weight other fibers having a fineness of more then 1.0 dtex and a length of at least 30 mm, said other fibers being predominantly located on the side of the topsheet facing the absorbent structure, while the side of the topsheet facing the wearer predominantly comprises microfibers.

DEFINITIONS

The term "microfibers" as used herein refers to small diameter fineness having a fineness of 1.0 dtex or less, which corresponds to 0.9 denier or less. The microfibers are manmade fibers of polymeric materials, such as polyolefins, polyamides, polyesters, regenerated cellulose fibers like rayon, lyocell, viscose etc.

The terms "hydrophilic" means fibers that are wetted by aqueous fluids in contact with the fibers. The degree of wetting of the fibers is described in terms of wetting angles.

Equipment suitable for measuring the wetting angles of particular fiber materials can be provided by Cahn SFA-222 Surface Force Analyzer System. When measured with this system, fibers having a contact angle for water less than 90 degrees are designated wettable and "hydrophilic", while fibers having a contact angle of more than 90 degrees are designated "hydrophobic".

The term "carded web" refers to a fibrous web made from staple length fibers sent through a combing or carding unit, which separates or breaks apart and aligns the staple fibers in machine direction (MD) to form a generally machine-direction oriented fibrous nonwoven layer.

The term "hydroentangling" involves forming a fibrous web, either drylaid or wetlaid, and entangling the fibrous web by means of very fine water jets under high pressure. Several rows of water jets are directed against the fibrous web which is supported by a movable wire or perforated drum.

The term "apertures" used in this context refers to apertures having an area of at least 0.1 $mm^2$ formed during hydroentangling.

The term "absorbent article" refers to products that are placed against the skin of the wearer to absorb and contain body exudates, like urine, faeces and menstrual fluid. The invention mainly refers to disposable absorbent articles, which means articles that are not intended to be laundered or otherwise restored or reused as an absorbent article after use. Examples of disposable absorbent articles include feminine hygiene products such as sanitary napkins, panty liners, tampons and sanitary panties; diapers and pant diapers for infants and incontinent adults; incontinence pads; diaper inserts and the like.

DETAILED DESCRIPTION OF THE INVENTION

Figure 1:
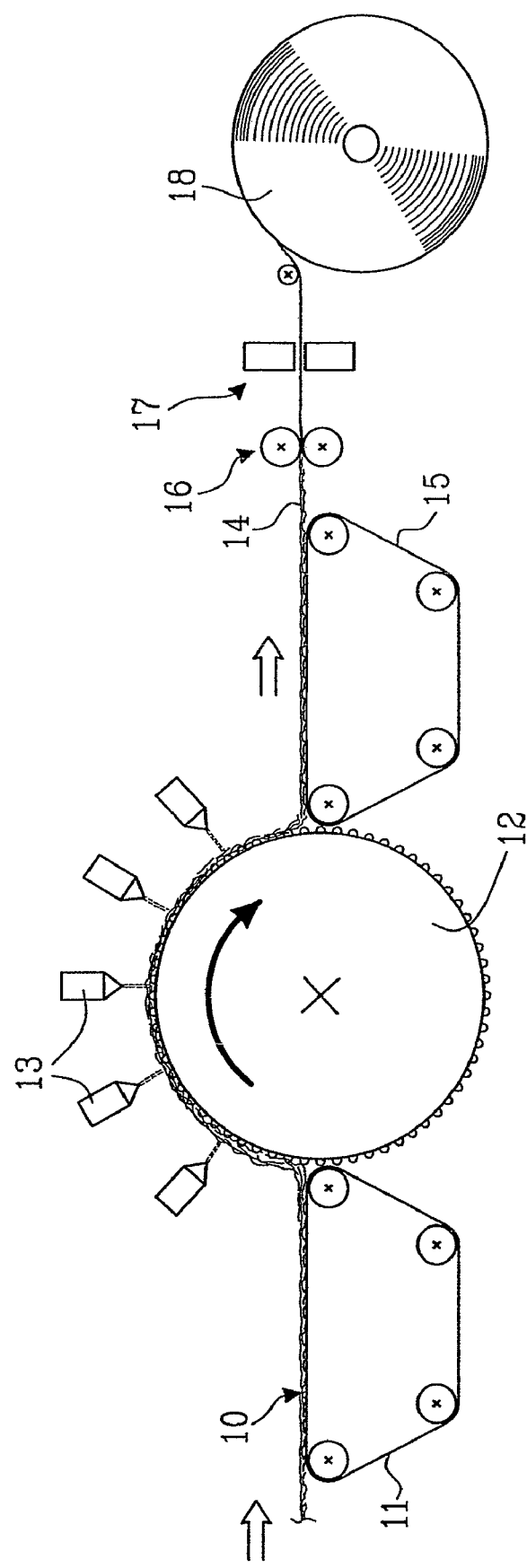
FIG. 1 illustrates schematically an apparatus for making a hydroentangled nonwoven fabric according to the invention.
Figure 2:
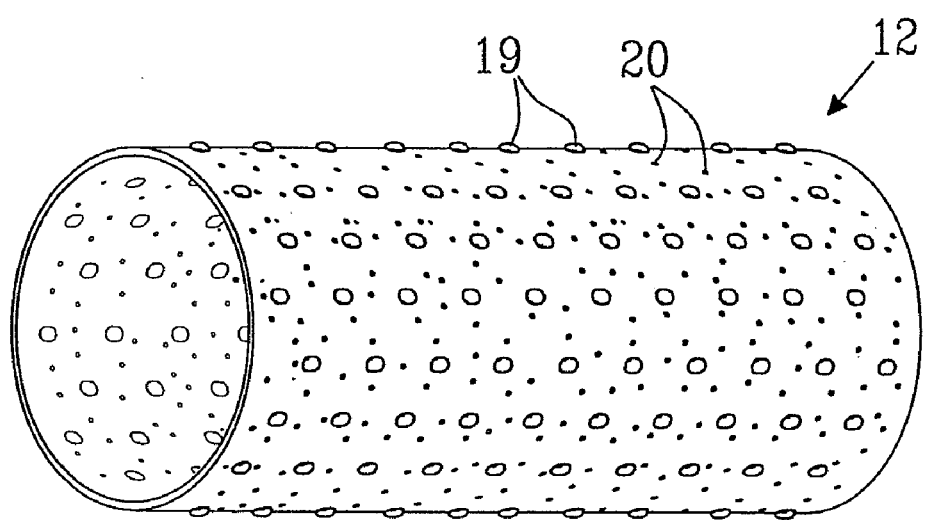
FIG. 2 is perspective view showing one example of a hydroentanglement support member adapted to produce apertured fabrics.

FIG. 1 shows schematically an apparatus for producing an apertured hydroentangled nonwoven material. A web 10 of fibres is advanced on a belt conveyor 11 to a hydroentangling station comprising a support member 12, in the form of a perforated drum, and a plurality of nozzles 13 from which water jets of high pressure are directed against the web 10. The nozzles are arranged in rows transversely across the web 10 so as to cover the width of the web. 10. The water jets accomplish an entanglement of the fibrous web, i.e. an intertwining of the fibres.

The pressure at the hydroentangling is preferably within the range 70 to 120 bars.

The web 10 of fibres is according to a preferred embodiment of the invention a carded web comprising at least 50%, preferably at least 70%, and up to 100% microfibers having a fineness of 1.0 dtex or less and a length of at least 30 mm, preferably at least 32 mm and more preferably at least 35 mm. It is further preferred that the maximum length of the microfibers is 70 mm. The carded web may be slightly bonded, such as by so called through-air-bonding, or non-bonded, when entering the hydroentangling station.

The microfibers are of manmade polymeric materials, such as polyolefins, polyamides, polyesters, regenerated cellulose fibers like rayon, lyocell and viscose etc. Preferably they are from hydrophobic polymers like polyolefins, polyamides and polyesters. Examples of suitable polymers are polypropylene (PP) and polyester (PET).

The microfibers or at least a proportion thereof may be crimped microfibers. The term "crimped" means that the microfibers have a wavy structure and thus are not completely straight.

A proportion of coarser fibres having a fineness of more than 1.0 dtex and up to 5.0 dtex, preferably in the range 2-4 dtex, may according to one embodiment be present in the web. These coarser fibres, if present, are preferably located on one side of the web as will be discussed below. In another embodiment the web contains no coarser fibres, thus all fibres being microfibres. The length of these coarser fibers is preferably within the same ranges as for the microfibers.

When producing fabrics containing both microfibers and coarser fibers in a layered configuration, a bilayer web is formed wherein one layer contains the microfibers and one layer contains the coarser fibers. The two layers are then mechanically combined during hydroentanglement, while maintaining a bilayer structure with predominantly microfibers on one surface and coarser fibers on the opposite surface.

The web is preferably free from natural fibres, such as wood pulp fibres.

The hydroentangled web 14 is drained over suction boxes (not shown) and via a belt conveyor 15 advanced through squeeze rollers 16 and a drying station 17 for further processing or winding on a storage roll 18. The apparatus may comprise additional hydroentangling stations, for example entangling the fibrous web from the opposite side thereof. This is well-known in the art.

During hydroentangling apertures are formed in the web 10 by using a support member 12 especially designed for this. In the embodiment shown in FIG. 1 a support member is in the form of a drum having a plurality of bosses 19 projecting from the surface of the drum. A plurality of drainage holes 20 are provided in the areas between the bosses 19. It would also be possible to have drainage holes in the area of the bosses 19 as well. A further description of drums adapted to produce apertured hydroentangled nonwoven fabrics is found in e.g. EP-A-0 223 614.

It is also possible to use other types of support members 12 than drums to produce apertured fabrics, such as wires having a coarse three-dimensional weave pattern or moulded, close-meshed screens as disclosed in WO 01/88261.

Apertures of different sizes may be produced in the web by having a varying three-dimensional structure of the support member 12 which will produce apertures of varying sizes. Apertures of different sizes arranged in discrete areas of the web, either in a repeated pattern in the machine direction of the web or in the cross direction may be produced by a support member 12 having a varying three-dimensional structure in machine direction or cross direction respectively, or both in machine and cross direction.

Figure 3:
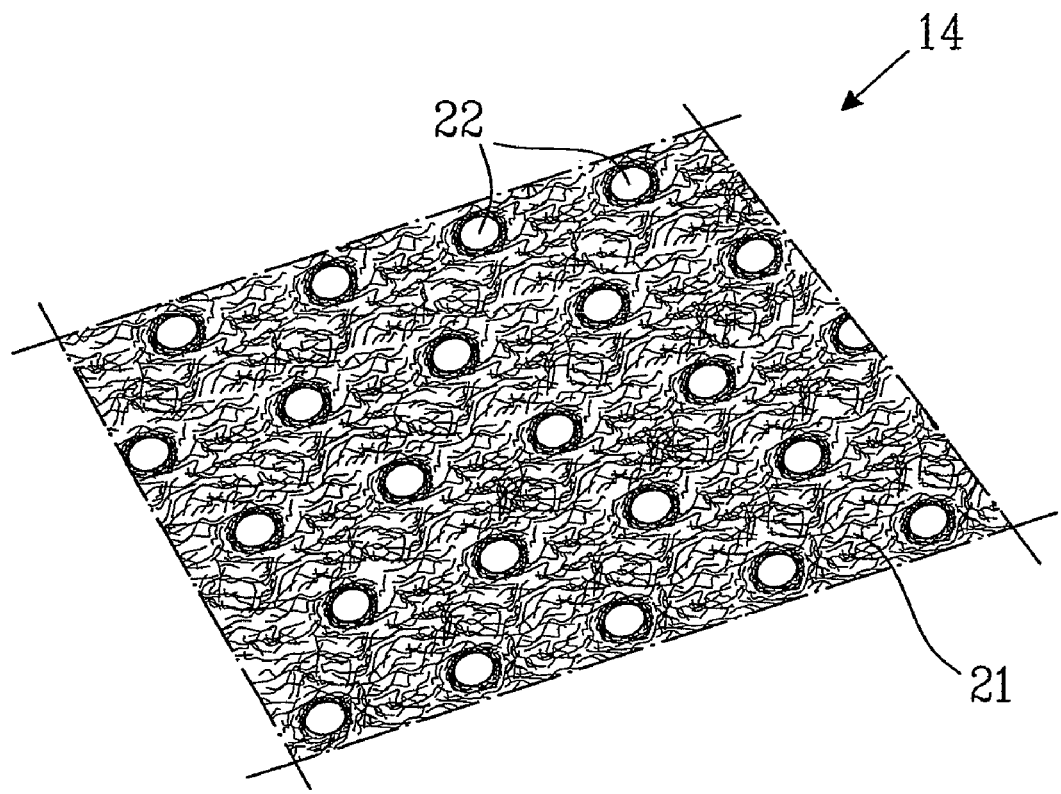
FIG. 3 is a perspective view on an enlarged scale of an apertured nonwoven fabric.

FIG. 3 illustrates an apertured nonwoven fabric 14 according to the invention comprising a carded web of microfibers 21 having been hydroentangled. The web comprises a plurality of apertures 22 produced by hydroentangling as described above.

Figure 4:
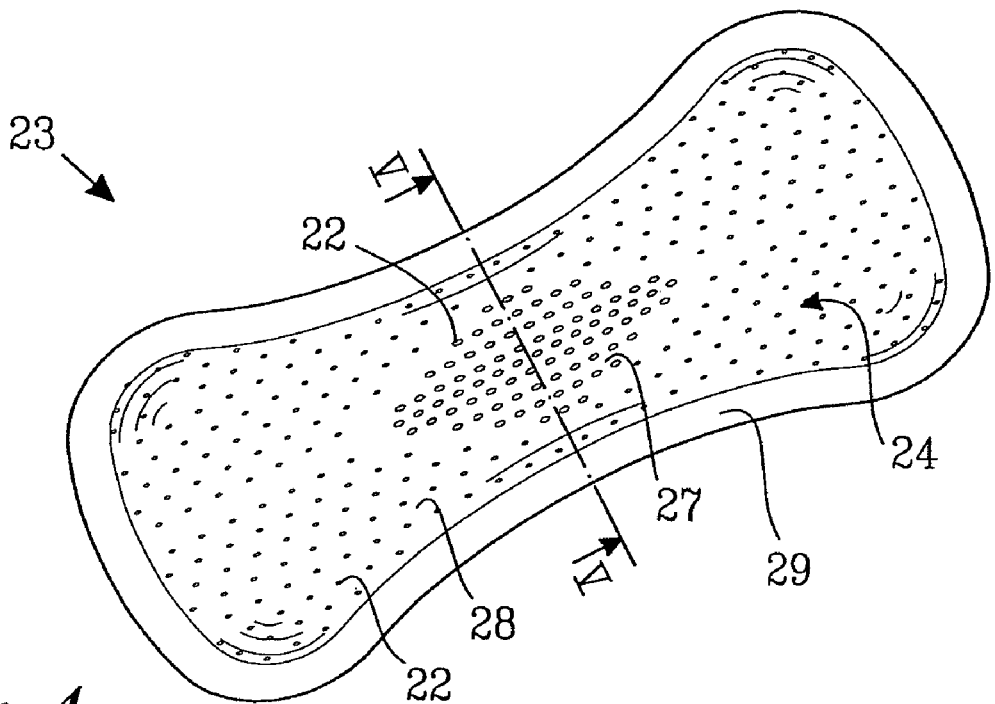
FIG. 4 is a plan view of an illustrative example of an absorbent product, such as a sanitary napkin, diaper, panty liner, incontinence guard and the like suitable for the present invention.
Figure 5:
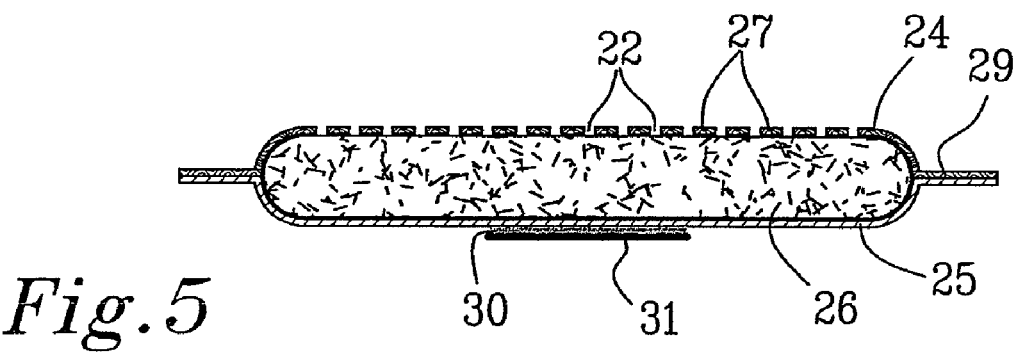
FIG. 5 is a cross sectional view through the absorbent article according to the line IV-IV in FIG. 4.

FIG. 4 shows an embodiment of an absorbent article in the form of a sanitary napkin 23 which typically comprises a liquid permeable topsheet 24, a liquid impermeable backsheet 25 and an absorbent core 26 enclosed therebetween. The liquid permeable topsheet 24 should be soft and non-irritating to the skin and be readily penetrated by body fluid, e.g. urine or menstrual fluid. According to the invention the liquid permeable topsheet is a hydroentangled nonwoven fabric comprising microfibers 21 as described above. The fabric is preferably apertured. As shown in FIG. 4 apertures 22 of different sizes are arranged in discrete areas of the topsheet 24. Thus the in the central portion 27 of the article, in which discharged body fluid will enter the article, the topsheet 24 comprises apertures that are larger than the apertures located in the surrounding portions 28 of the article. In an alternative embodiment selected areas, such as the areas adjacent the edges of the article, are free from apertures. In a further embodiment the topsheet is apertured only in the central area of the article. In a still further embodiment all apertures of the same size.

The size of the apertures 22 may vary from 0.1 to 8 mm$^2$, preferably between 0.8 and 4 mm$^2$. The total void area of the topsheet 24 in the apertured parts thereof relative to the total area of said part is between 10 and 50%, preferably between 20 and 40%.

The topsheet 24 has a basis weight between 16 and 60 g/m$^2$, preferably between 20 and 40 g/m$^2$. It may contain up to 100% microfibers or may contain a certain amount, up to 50% by weight, of other man made fibers, having a fineness above 1.0 dtex. If such coarser fibers are present they are preferably mainly located on the side of the topsheet 24 facing away from the wearer. The microfibers and/or the coarser fibers, if present, or at least a portion of the microfibers or coarser fibers may be crimped fibers.

The topsheet 24 may be treated with a wetting agent.

The liquid impermeable backsheet 25 of the article may consist of a thin plastic film, e.g. a polyethylene or polypropylene film, a nonwoven material coated with a liquid impervious material, a hydrophobic nonwoven material, which resists liquid penetration or laminates of plastic films and nonwoven materials. The backsheet material 25 may be breathable so as to allow vapour to escape from the absorbent core, while still preventing liquids from passing through the backsheet material.

The topsheet 24 and the backsheet material 25 have a somewhat greater extension in the plane than the absorbent core 26 and extend outside the edges thereof. The topsheet 24 and backsheet 25 are connected to each other within the projecting portions 29 thereof, e.g. by gluing or welding by heat or ultrasonic. The topsheet and/or the backsheet may further be attached to the absorbent core by any method known in the art, such as adhesive, heat bonding etc. The absorbent core may also be unattached to the topsheet and/or the backsheet.

A fastening means in the form of a region 30 of an adhesive is provided on the side of the backsheet 25 facing away from the wearer in use. The adhesive may releasably attach to the undergarment of the wearer. A release paper 31 protects the adhesive region 30 before use. The adhesive region 30 may have any suitable configuration, such as elongate or transverse strips, dots, full-coated areas etc.

In other embodiments of the invention other types of fasteners, like friction fasteners, tape tabs or mechanical fasteners like hook-and-loop fasteners etc. may be used to fasten the articles to the underwear or around the waist of the wearer. Some absorbent articles are in the form of pants and therefore do not need special fastening means. In other cases the absorbent article is worn in special elastic pants without the need for additional fasteners.

The absorbent body 26 can be of any conventional kind. Examples of commonly occurring absorbent materials are cellulosic fluff pulp, tissue layers, airlaid cellulose material, highly absorbent polymers (so called superabsorbents), absorbent foam materials, absorbent nonwoven materials or the like. It is common to combine cellulosic fibers with superabsorbents in an absorbent body. It is also common to have absorbent bodies comprising layers of different material with different properties with respect to liquid acquisition capacity, liquid distribution capacity and storage capacity. This is well-known to the person skilled in the art and does therefore not have to be described in detail. The thin absorbent bodies, which are common in today's absorbent articles, often comprise a compressed mixed or layered structure of cellulosic fibers and superabsorbent material. The size and absorbent capacity of the absorbent core may be varied to be suited for different uses such as sanitary napkins, pantiliners, adult incontinence pads and diapers, baby diapers, pant diapers, etc.

Test Results

Tests have been performed with respect to rewet and liquid inlet time for some different nonwoven fabrics. The fabrics had the following characteristics:

Sample A: A carded hydroentangled fabric, basis weight 30 gsm, PET microfibers having a fineness of 0.99 dtex and a length of 38 mm, no apertures, wetting agent: Synthesin 7290 0.5%, supplier Dr Th Böhme KG.

Sample B: A carded hydroentangled fabric, basis weight 50 gsm, PET microfibers having a fineness of 0.99 dtex and a length of 38 mm, no apertures, wetting agent: same as for sample A.

Sample C: A carded hydroentangled fabric, basis weight 25 gsm, PET microfibers having a fineness of 0.99 dtex and a length of 38 mm, apertures 3.2 mm$^2$, open area 13%, wetting agent: same as for sample A.

Sample D: A carded hydroentangled fabric, basis weight 50 gsm, PET microfibers having a fineness of 0.99 dtex and a length of 38 mm, apertures 3.2 mm$^2$, open area 13%, wetting agent: same as for sample A.

Sample E: A reference material in the form of a spunbond material, basis weight 48 gsm, PP fibers of a fineness of 3.0 dtex, no apertures, wetting agent: same as for sample A.

The methods used in the tests are described below:

Rewet

This method is designed to determine a sanitary towel's ability to retain an amount of fluid.

Apparatus

Metering equipment, Dosimat 665
Fluid pipe.
Stopwatch, accuracy 0.1 s
Timer, accuracy 1 s
Balance, accuracy 0.01 g
Loading weights, 900 g, (Ø 48 mm=18.09 cm2), measurement pressure ~5 kPa
Filter paper, Ø 48 mm, grade 2282, from Schleicher & Schuell
Synthetic menstrual fluid Sample Preparation The products should be laboratory conditioned and should be representative of the batch to which the test relates.

Procedure

Check that the temperature of the test fluid is between 23+1/−2° C.
Put the sanitary towel flat on the table and lower the fluid pipe under a static load of 2±0.1 N.
Fix the Dosimat hose inside the fluid pipe.
Dosimat settings: 1 ml/min 15 ml
Start the test equipment with a dynamic load. Start the timer, set at 45 minutes, and the Dosimat simultaneously.
Turn off the test equipment after 15 minutes, when the metering process is finished, and remove the sanitary Towel After a further 30 minutes: Put five filter papers on the balance and tare it. Centre the five filter papers above the wetting point. Put the weight carefully on top of the filter papers and start the stopwatch.
Remove the filter papers after exactly 15 seconds.
Weigh the filter papers on the tared balance and note the rewetting, accuracy 0.01 g.

Inlet Time

Figure 6:
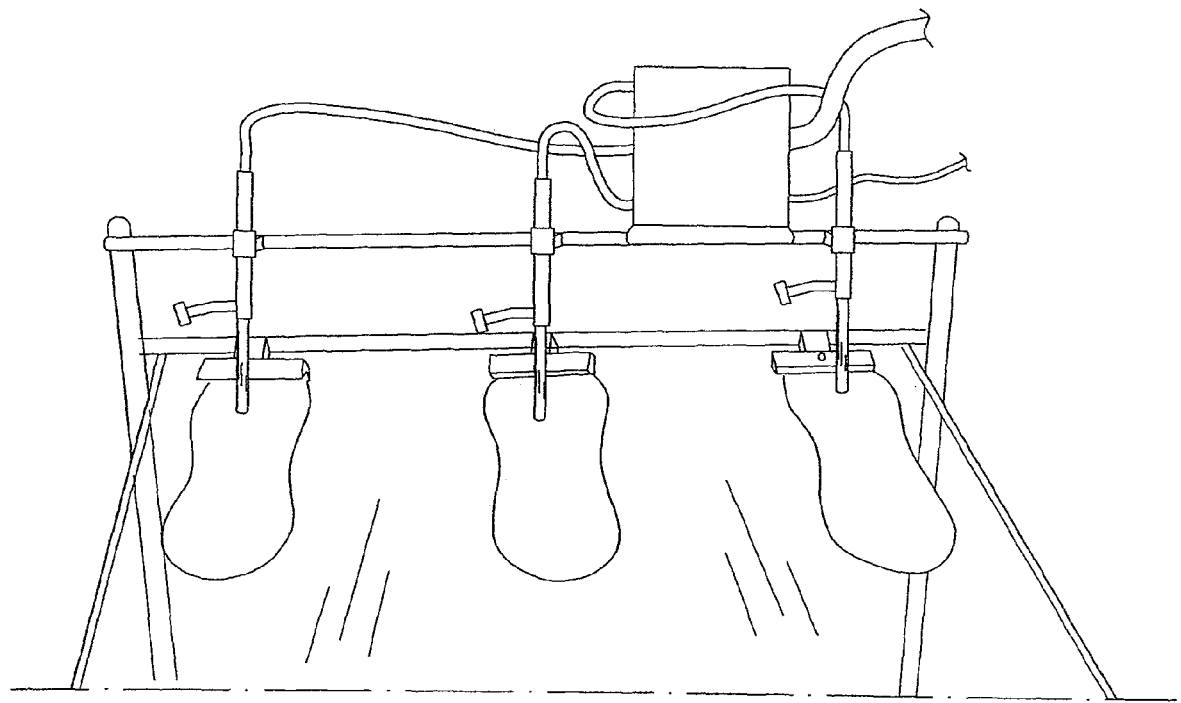
FIGS. 6, 7 and 8 illustrate the test method for measuring inlet time.
Figure 7:
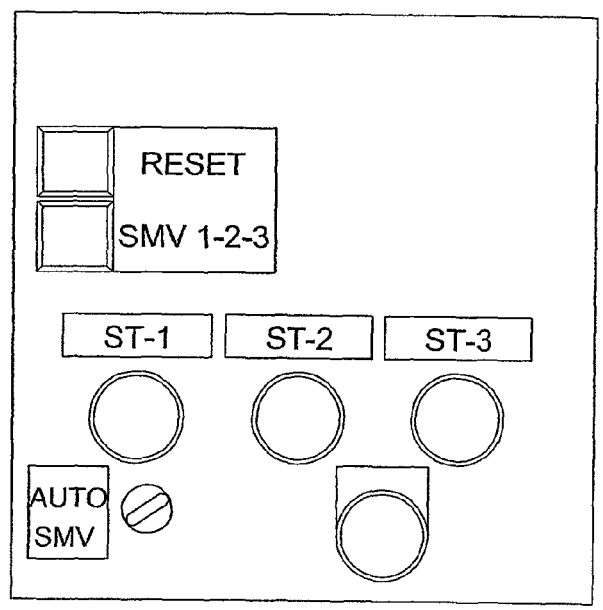
Figure 8:
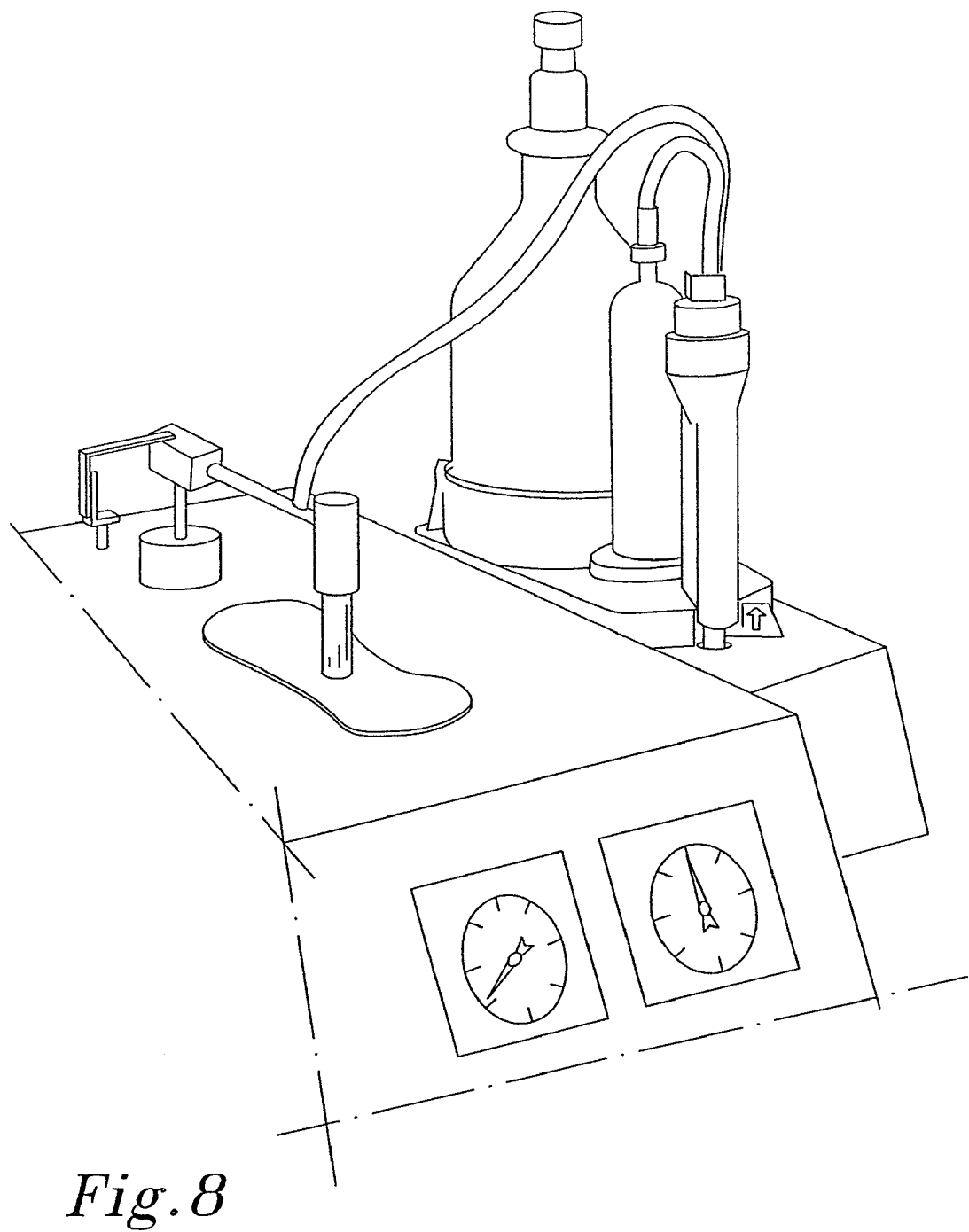

This method illustrated by photos FIGS. 6, 7 and 8 aims to evaluate the penetration of a complete product when synthetic menstrual fluid is poured onto the product, which has been placed on a sloping surface.

Principle

To measure the penetration time.

Apparatus

Plexiglass table with an angle of 25°,
Stand with clamps to hold the products in place,
Glass tube
Dosimat connected to the glass tube, inner diameter 2.9 mm.
Timer, accuracy ±0.3 s
Stopwatch, accuracy ±0.3 s
Synthetic menstrual fluid Settings Flow speed: 20 ml/min
Doses: 5 ml
Angle of plexiglass table 250
The glass tube should be positioned vertically, i.e. 1150 from the sloping plexiglass slab. See FIG. 8.

Sample Preparation

Procedure

Attach the product with the clip so that the glass tube is about 10 mm inside the absorption core.
Adjust the product so that it is positioned straight.
Adjust the distance between the mouth of the glass tube and the product to 10 mm.
Start the timer and the Dosimat at the same time.
When the fluid has been added measure the time it takes for the fluid to penetrate the surface material with the stop watch.
After five minutes, repeat the procedure from point 4. The procedure should be repeated twice, i.e. three batches of fluid.

The test results are presented in Table 1.

TABLE 1

| Sample | Rewet (g) | Inlet time 1 (s) | Inlet time 2 (s) | Inlet time 3 (s) |
|---|---|---|---|---|
| A | 0.83 | 1.48 | 5.14 | 8.36 |
| B | 1.05 | 1.89 | 5.28 | 8.67 |
| C | 0.62 | 0.90 | 2.12 | 3.59 |
| D | 0.30 | 1.28 | 2.79 | 4.96 |
| E | 0.48 | 1.33 | 3.36 | 4.91 |

The test values given are mean values for six measurements.

It can be concluded that for the microfiber nonwoven materials aperturing seems to be of importance both for obtaining a quick inlet time and a low rewet.

It is understood that the invention is not limited to the embodiments described above and shown in the drawings, but can be modified within the scope of the claims.

The invention claimed is:

1. A nonwoven fabric comprising
microfibers having a fineness of 1.0 dtex or less and having been combined by hydroentangling, said fabric being apertured by said hydroentangling, wherein the fabric comprises at least 50% by weight of said microfibers, which have a length of at least 30 mm and have been carded before hydroentangling;
a plurality of first apertures of a first size disposed in a first zone; and
a plurality of second apertures of a second size disposed in a second zone surrounding the first zone,
wherein the fabric contains an amount of crimped microfibers.

2. The fabric of claim 1, wherein the nonwoven fabric comprises at least 70% of said microfibers.

3. The fabric of claim 1, wherein the nonwoven fabric comprises 100% manmade fibers and is free from natural fibers.

4. The fabric of claim 3, wherein the nonwoven fabric comprises 100% of said microfibers.

5. The fabric of claim 1, wherein the microfibers have a length of at least 32 mm.

6. The fabric of claim 1, wherein the plurality of first apertures of the first size in the first zone and the plurality of second apertures of the second size in the second zone surrounding the first zone are in a repeated pattern in at least one of a machine direction, a cross direction of the fabric, and both in the machine and the cross direction.

7. The fabric of claim 1, wherein a size of each aperture may vary from 0.1 to 8 mm$^2$.

8. The fabric claim 1, wherein an open area of the apertured fabric is between 10 and 50%.

9. The fabric of claim 1, wherein the fabric has a basis weight of between 16 and 60 g/m$^2$.

10. The fabric of claim 1, wherein all microfibers are hydrophobic microfibers.

11. The fabric of claim 10, wherein the fabric contains a wetting agent.

12. The fabric of claim 1, wherein the fabric comprises up to 50% by weight man made fibers having a fineness of more than 1.0 dtex and up to 5.0 dtex.

13. The fabric of claim 12, wherein said fibers having a fineness of more than 1.0 dtex are predominantly located on one side of the fabric, while an opposite side of the fabric predominantly comprises microfibers.

14. A method of making a nonwoven fabric, comprising the steps of:
forming a carded fibrous web comprising at least 50% by weight microfibers having a fineness of 1.0 dtex or less and a length of at least 30 mm;
hydroentangling the carded fibrous web using an aperturing support member to produce an apertured hydroentangled nonwoven fabric;
forming a plurality of first apertures of a first size disposed in a first zone; and
forming a plurality of second apertures of a second size disposed in a second zone surrounding the first zone,
wherein the fabric contains an amount of crimped microfibers.

15. The method as claimed in claim 14, wherein the aperturing support member forms the plurality of first apertures of the first size disposed in the first zone and the plurality of second apertures of the second size disposed in the second zone surrounding the first zone in a repeated pattern in at least one of a machine direction, a cross direction of the web, and both in the machine and the cross direction.

16. The method as claimed in claim 14, wherein the carded fibrous web comprises at least 50% by weight microfibers and no more than 50% by weight other fibers having a fineness of more then 1.0 dtex and a length of at least 30 mm, wherein said microfibers and other fibers are applied in a layered configuration, and wherein the hydroentangled nonwoven fabric produced by hydroentangling the carded fibrous web comprises predominantly microfibers on one side and predominantly other fibers on the opposite side.

17. The method as claimed in claim 14, comprising hydroentangling the carded fibrous web with a hydroentangling pressure of between 70 and 120 bars.

18. Absorbent article comprising a topsheet arranged on a wearer facing side of an absorbent structure wherein said topsheet comprises a carded, hydroentangled and apertured nonwoven fabric as claimed in claim 1,
wherein said topsheet comprises apertures of at least two different sizes arranged in discrete zones of the topsheet, and
wherein apertures of a relatively larger size are arranged in a central portion of the article intended to form a wetting area, while apertures of a relatively smaller size are arranged in an area surrounding the wetting area.

19. Absorbent article as claimed in claim 18, wherein said nonwoven fabric forming the topsheet comprises no more than 50% by weight other fibers having a fineness of more then 1.0 dtex and a length of at least 30 mm, said other fibers being predominantly located on a side of the topsheet facing the absorbent structure, while a side of the topsheet facing a wearer predominantly comprises microfibers.

20. The fabric of claim 2, wherein the nonwoven fabric comprises at least 90% of said microfibers.

21. The fabric of claim 5, wherein the microfibers have a length of at least 35 mm.

22. The fabric of claim 7, wherein the size of each aperture varies from between 0.8 and 4 mm$^2$.

23. The fabric of claim 8, wherein the open area of the apertured fabric is between 20 and 40%.

24. The fabric of claim 9, wherein the basis weight is between 20 and 40 g/m$^2$.

25. The fabric of claim 12, wherein the fineness is between 2.0 and 4.0 dtex.

26. The method as claimed in claim 14, wherein the length of the microfibers is at least 32 mm.

27. The method as claimed in claim 26, wherein the length of the microfibers is at least 35 mm.

* * * * *